(12) United States Patent
Carpenter et al.

(10) Patent No.: US 7,566,573 B2
(45) Date of Patent: Jul. 28, 2009

(54) DUAL STANDARD CURVE IMMUNOASSAY

(75) Inventors: Charles R. Carpenter, Scarborough, ME (US); Giosi Farace, Georgetown, ME (US); Paul Scott MacHenry, Portland, ME (US); Brian John Foster, Portland, ME (US); Mirolee Blue Zieba, Westbrook, ME (US); Michael Ryan D'Angelo, Scarborough, ME (US)

(73) Assignee: Idexx Laboratories, Inc., Westbrook, ME (US)

( * ) Notice: Subject to any disclaimer, the term of this patent is extended or adjusted under 35 U.S.C. 154(b) by 375 days.

(21) Appl. No.: 11/311,567

(22) Filed: Dec. 19, 2005

(65) Prior Publication Data

US 2007/0141717 A1    Jun. 21, 2007

(51) Int. Cl.
*G01N 33/541*  (2006.01)
*G01N 33/533*  (2006.01)
*G01N 33/543*  (2006.01)

(52) U.S. Cl. .................. 436/540; 435/7.1; 436/518

(58) Field of Classification Search ...................... None
See application file for complete search history.

(56) References Cited

U.S. PATENT DOCUMENTS

| | | | | |
|---|---|---|---|---|
| 4,487,830 A | * | 12/1984 | Coates et al. | 435/7.23 |
| 4,595,661 A | * | 6/1986 | Cragle et al. | 435/7.94 |
| 4,777,133 A | * | 10/1988 | Picciolo et al. | 435/7.22 |
| 5,656,207 A | | 8/1997 | Woodhead et al. | 252/700 |
| 5,672,475 A | | 9/1997 | Lee et al. | 435/6 |
| 5,922,558 A | | 7/1999 | Akhavan-Tafti | |
| 2004/0171091 A1 | * | 9/2004 | Lesko et al. | 435/7.23 |

FOREIGN PATENT DOCUMENTS

WO           9403811         2/1994

OTHER PUBLICATIONS

Mosedale et al. "Optimization of immunofluorescence methods by quantitative image analysis" J Histochem Cytochem. 1996 Sep. 1996;44(9):1043-50.*
Burtis, C.A. (Ed.), Tietz Textbook of Clinical Chemistry, 3rd Edition ('999), W.B. Saunders Company, Philadelphia, PA, pp. 218-220.*
www.appliedbiosystems.com, *Applied Biosystems 1700 Chemiluminescent Microarray Analyzer*, 2004.
Christofides, N., et al., *Enhanced Chemiluminescence labeled-Antibody Immunoassay (Amerlite-MAB™) for Free Thyroxine: Design, Development and Technical Validation*, Clinical Chemistry, 4:17-23 (1995).
Midgley, John E., *Direct and Indirect Free Thyroxine Assay Methods: Theory and Practice*, Clinical Chemistry, 47:1353-1363 (2001).
Kopf, Eliezer, et al., *Panorama Mouse/Rat Tissue Extract Protein Array Kit: A New Tool for Protein Expression Analysis*, Application Notes, 2005, 12-15, www.sigmaaldrich.com.
Thermo Fisher Scientific, Inc., *Developing an ELISA*, 2008, www.piercenet.com.
Assay Designs, Catalog, *Correlate Colorimetric & Chemiluminescent Assay Formats*, 1998, pp. 1-3.
Assay Designs, Package Insert for BIOTREND *Correlate Colorimetric & Chemiluminescent Assay Formats*.
Applied Biosystems, Applied Biosystems 1700 Chemiluminescent Microarray Analyzer, 2004, www.appliedbiosystems.com.
Vector Laboratories, Package Insert/Protocol for *DuoLuX Chemiluminescent/Fluorescent Substrate for Alkaline Phosptase*, 2001, 1-4, www.vectorlabs.com.

* cited by examiner

*Primary Examiner*—Christopher L Chin
*Assistant Examiner*—Christine Foster
(74) *Attorney, Agent, or Firm*—McDonnell Boehnen Hulbert & Berghoff LLP

(57) ABSTRACT

A method and a kit for determining the presence or amount of analytes in samples over a broad potential concentration range for the analyte. The method and kit incorporate chemiluminescent and fluorescent labels conjugated to a specific binding partner for the analyte for sandwich assays, or to the analyte or an analog of the analyte for competitive assays. The conjugates are mixed with the sample and the labels are detected simultaneously or sequentially.

7 Claims, 3 Drawing Sheets

50% of maximum signal = 2.6μg/dL

50% of maximum signal = 0.35μg/dL

DUAL STANDARD CURVE IMMUNOASSAY

BACKGROUND OF THE INVENTION

1. Field of the Invention

In general, the invention relates to the detection of analytes in samples. More specifically, the invention relates to the detection of analytes using more than one label to detect the analyte over a broad concentration range.

2. Description of Related Art

Various analytical procedures and devices are commonly employed in specific binding assays to determine the presence and/or amount of substances of interest or clinical significance which may be present in biological or non-biological fluids. Such substances are commonly termed "analytes" and can include, for example, antibodies, proteins, drugs, hormones, cells, and nucleic acids.

Specific binding assays incorporate specific binding members, typified by antibody and antigen immunoreactants, wherein one member of the specific binding pair is labeled with a signal-producing compound (e.g., an antibody or an antigen labeled with an enzyme, a fluorescent compound, a chemiluminescent compound, a radioactive isotope, a direct visual label, etc.). Typically in a sandwich assay the test sample suspected of containing analyte can be mixed with a labeled anti-analyte antibody, i.e., conjugate, and incubated for a period of time sufficient for the immunoreaction to occur. The reaction mixture is subsequently analyzed to detect either that label which is associated with an analyte/conjugate complex (bound conjugate) or that label which is not complexed with analyte (free conjugate). As a result, the amount of label in one of these species can be correlated to the amount of analyte in the test sample. In a competitive assay the test sample is mixed with either a labeled antigen or a labeled antigen analog and these labeled compounds compete with the analyte in the test sample for binding sites on the antibody. The ratio of labeled compound versus test compound determines the level of signal obtained. High analyte concentrations in the test material will result in low signals and vice versa.

Analytes may be present in samples over a broad concentration range. For example, T4 is produced by the thyroid in mammals. A high concentrations of T4 in the blood stream is a marker for hyperthyroidic conditions, and a low concentrations is a marker for hypothyroidic conditions. The difference in T4 concentration between hyperthyroidic and hypothyroidic conditions can be as great as ten fold. Numerous other analytes may be present in biological samples in broad concentration ranges, for example, drugs of abuse, therapeutic drugs, cortisol, HGH, HCG, LSH, TSH, the TORCH panel antigens and the like. While several types of detection systems are available, no one system has been able to simply and easily measure a broad concentration range of T4 or other analytes that may be present in the blood or other samples without resorting to some form of mathematical manipulation. These manipulations include, for example, the use of multiple standard curves to standardize the entire concentration range, or use of some form of a 'fudge' factor to alter the standard curve at different points across the concentration range. Alternatively the assay conditions may be altered so that differently optimized assays are run at different points through the concentration range.

SUMMARY OF THE INVENTION

In one aspect, the invention is directed to a method for determining the presence or amount of an analyte in a sample. The method includes providing a quantity of a first specific binding partner for the analyte, labeling a first portion of the quantity of the first specific binding partner with a chemiluminescent label, and labeling a second portion of the quantity of the first specific binding partner with a fluorescent label. After the sample is mixed with the first and second portions, the association of the fluorescent label and the chemiluminescent label with the analyte is detected, which allows for the determination of the presence or amount of the analyte in the sample.

In another aspect of the invention, the method includes forming a mixture of the sample with (1) the analyte or an analyte analog conjugated to a chemiluminescent label and (2) the analyte or an analyte analog conjugated to a fluorescent label. The mixture is contacted with a specific binding partner for the analyte. The association of the fluorescent label and the chemiluminescent label with the specific binding partner for the analyte is detected, which allows for the determination the presence or amount of analyte in a sample.

In a further aspect, the invention is directed to a kit for the detection of an analyte in a sample. The kit includes a first portion of a quantity of a first specific binding partner conjugated to a chemiluminescent label, a second portion of the quantity of the first specific binding partner conjugated to a fluorescent label, and instructions for conducting an assay using the first portion and the second portion to detect the analyte.

In another aspect, the kit includes a first portion of a quantity of the analyte or an analyte analog conjugated to a chemiluminescent label, a second portion of the quantity of the analyte or the analyte analog conjugated to a fluorescent label; and instructions for conducting an assay using the first portion and the second portion to detect the analyte.

DETAILED DESCRIPTION

Figure 1:
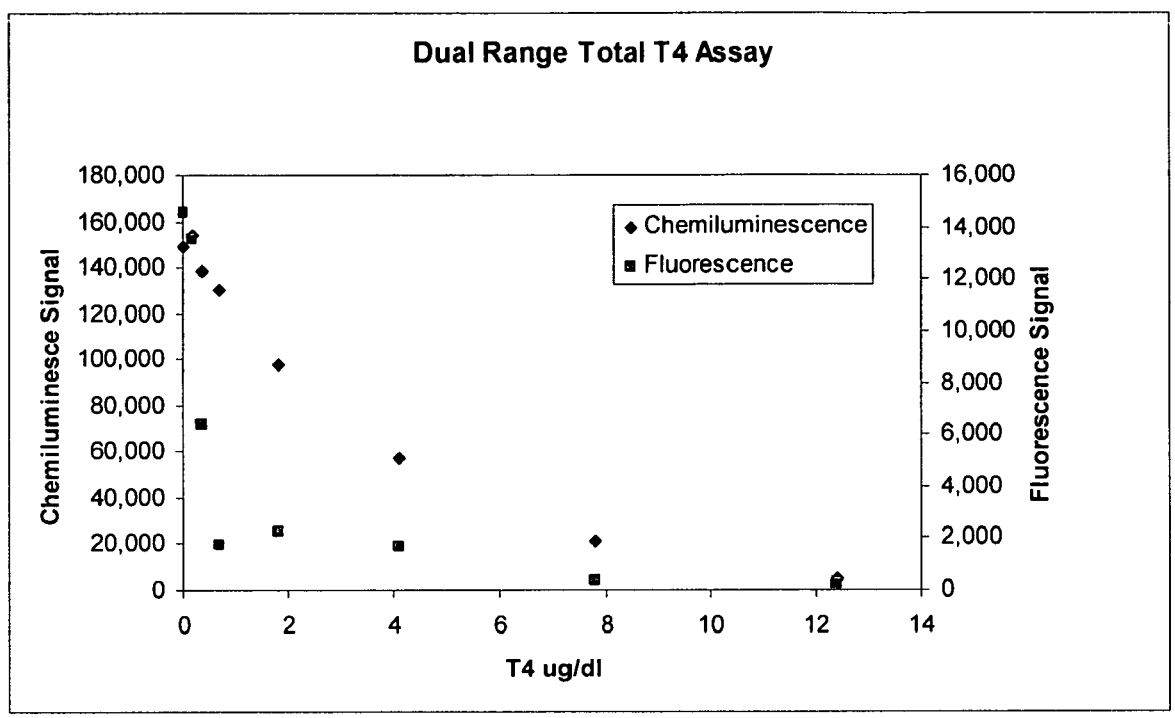
FIG. 1 is a graph showing both the chemiluminescent and fluorescent signals obtained in a T4 assay of samples having various T4 concentrations using the method of the present invention.

In general, the present invention is directed to an immunological method of detecting the quantity of an analyte in a sample over a broad range of analyte concentrations. In one aspect, analytes are detected by using a binding partner for analyte, where separate aliquots of the same binding partner have different labels. A first quantity of the specific binding partner is labeled with a fluorescent label and the second quantity is labeled with a chemiluminescent label. Both of the labeled quantities are mixed with the sample. Detection of the analyte in the sample is accomplished by detecting the association of the labels and the analyte.

Before describing the present invention in detail, a number of terms will be defined. As used herein, the singular forms "a," "an", and "the" include plural referents By "analyte" is meant a molecule or substance to be detected. For example, an analyte, as used herein, may be a ligand, which is mono- or polyepitopic, antigenic or haptenic;

it may be a single compound or plurality of compounds that share at least one common epitopic site; it may also be a receptor or an antibody.

A "sample" refers to an aliquot of any matter containing, or suspected of containing, an analyte of interest. For example, samples include biological samples, such as samples from taken from animals (e.g., saliva, whole blood, serum, and plasma, urine, tears and the like), cell cultures, plants, etc.; environmental samples (e.g., water); and industrial samples. Samples may be required to be prepared prior to use in the methods of the invention. For example, samples may require diluting, filtering, centrifuging or stabilizing prior to use with the invention. For the purposes herein, "sample" refers to the either the raw sample or a sample that has been prepared.

"Binding specificity" or "specific binding" refers to the substantial recognition of a first molecule for a second molecule, for example a polypeptide and a polyclonal or monoclonal antibody, an antibody fragment (e.g. a Fv, single chain Fv, Fab', or F(ab')2 fragment) specific for the polypeptide, enzyme—substrate interactions, and polynucleotide hybridization interactions.

"Non-specific binding" refers to non-covalent binding between molecules that is relatively independent of specific surface structures. Non-specific binding may result from several factors including electrostatic and hydrophobic interactions between molecules.

"Member of a specific binding pair" or "specific binding partner" refers one of two different molecules, having an area on the surface or in a cavity which specifically binds to and is thereby defined as complementary with a particular spatial and polar organization of the other molecule. The members of the specific binding pair are referred to as ligand and receptor (antiligand). These will usually be members of an immunological pair such as antigen-antibody, although other specific binding pairs such as biotin-avidin, hormones-hormone receptors, IgG-protein A, polynucleotide pairs such as DNA-DNA, DNA-RNA, and the like are not immunological pairs but are included in the invention and the definition of specific binding pair member.

"Analyte-specific binding partner" refers to a specific binding partner that is specific for the analyte.

"Substantial binding" or "substantially bind" refer to an amount of specific binding or recognizing between molecules in an assay mixture under particular assay conditions. In its broadest aspect, substantial binding relates to the difference between a first molecule's incapability of binding or recognizing a second molecule, and the first molecules capability of binding or recognizing a third molecule, such that the difference is sufficient to allow a meaningful assay to be conducted distinguishing specific binding under a particular set of assay conditions, which includes the relative concentrations of the molecules, and the time and temperature of an incubation. In another aspect, one molecule is substantially incapable of binding or recognizing another molecule in a cross-reactivity sense where the first molecule exhibits a reactivity for a second molecule that is less than 25%, preferably less than 10%, more preferably less than 5% of the reactivity exhibited toward a third molecule under a particular set of assay conditions, which includes the relative concentration and incubation of the molecules. Specific binding can be tested using a number of widely known methods, e.g., an immunohistochemical assay, an enzyme-linked immunosorbent assay (ELISA), a radioimmunoassay (RIA), or a western blot assay.

"Ligand" refers any organic compound for which a receptor naturally exists or can be prepared.

"Analyte analog" or an "analog of the analyte" refers to a modified form of the analyte which can compete with the analyte for a receptor, the modification providing means to join the analyte to another molecule. The analyte analog will usually differ from the analyte by more than replacement of a hydrogen with a bond that links the analyte analog to a hub or label, but need not. The analyte analog can bind to the receptor in a manner similar to the analyte.

"Receptor" refers to any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, protein A, complement component $C1q$, and the like.

"Antibody" refers to an immunoglobulin that specifically binds to and is thereby defined as complementary with a particular spatial and polar organization of another molecule. The antibody can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and $F(ab')_2$, Fab', and the like. In addition, aggregates, polymers, and conjugates of immunoglobulins or their fragments can be used where appropriate so long as binding affinity for a particular molecule is maintained.

"Substrate" as used herein refers to a solid phase material to which another material binds or can be attached, for example, the interior surface of a capillary tube, a microtitre plate well, a porous matrix, a particle or other solid support. Generally a substrate can comprise a specific binding pair member, wherein the member can bind to a second member of the binding pair. For example, a substrate can be an antibody bound to a solid surface, wherein the antibody would be considered a capture binding member of a binding pair. The corresponding antigen would be a second binding member. Substrates can also include the antibody directly attached to the surface, either covalently or non-covalently.

A "label" is a molecule that is bound (via covalent or non-covalent means, alone or encapsulated) to another molecule or solid support and that is chosen for specific characteristics that allow detection of the labeled molecule. In one aspect the assay method of the invention employs two labels: a chemiluminescent label and a fluorescent label. For example, suitable fluorescent labels should be capable of conjugation with antigens, haptens or antibodies in order to be used in the labeled conjugate. Selection of the fluorescent label is based on synthetic convenience, emission maximum, quantum efficiency, stability under the assay conditions, and the like, but the particular fluorescent label is not critical, so long as there is a minimum quantum yield to provide the desired sensitivity. A large number of commercially available fluorescent labels can be employed. Illustrative fluorescent labels include fluorescein-isothiocyanate (FITC), rhodamine, Texas Red, phycoerythrin, Cy-5® and allophycoerythrin, and particularly, fluorescent labels that fluoresce above about 550 nm, more particularly, fluorescent labels that fluoresce above 600 nm, and efficiently absorb light having absorption above 500 nm; more particularly, 650 nm, such as Cy-5®.

Chemiluminescent labels include horseradish peroxidase (HRP), alkaline phosphatase, acridium esters and other well known labels. When the label on the conjugate reagent is an enzyme, the detection reagents may include a substrate which produces a detectable signal upon reaction with the enzyme in the detection zone. For example, the well-characterized enzyme horseradish peroxidase produces a colored product when reacted with the substrate, 4-chloro-1-napthol. One commercially-available substrate solution is TM Blue, which is available from TSI Incorporated (Worcester, Mass.). Also of interest are enzymes which involve the production of hydrogen peroxide and the use of the hydrogen peroxide to oxidize a dye precursor to a dye. Particular combinations include saccharide oxidases e.g., glucose and galactose oxidase, or heterocyclic oxidases, such as uricase and xanthine oxidase, coupled with an enzyme which employs the hydrogen peroxide to oxidize a dye precursor, e.g., peroxidase, microperoxidase, and cytochrome C oxidase. Other well known enzymatic reactions result in chemiluminescence (e.g., luminal and HRP) or fluorescence (e.g., methylumbelliferone and alkaline phosphatase) signals The labels can be conjugated to haptens, antibodies or other binding partners to form the labeled conjugate using any convenient method (see e.g. Harlow, E. & Lane, D. (1988) *Antibodies: A Laboratory Manual*, Cold Spring Harbor Laboratory, Cold Spring Harbor: N.Y.; Harlow, E. & Lane, D. (1999) *Using Antibodies: A Laboratory Manual*, Cold, Spring Harbor Laboratory Press, Cold Spring Harbor: N.Y.; Sambrook, J. et al. (1989) *Molecular Cloning: A Laboratory Manual*, Cold Spring Harbor Laboratory Press, Cold Spring Harbor: N.Y.; and the like). Generally, the label is conjugated to a specific binding partner. The attachment of the labels to the analyte-specific binding partners may be accomplished directly, through a linker, or through a pair of specific binding partners (e.g. biotin/avidin) as is well known in the art. Also included with the scope of the term conjugate is the attachment of both of the label and the specific binding partner to a particle.

The invention can be accomplished using the numerous immunoassay techniques known in the art that allows for the detection of the binding of the analyte to the labeled specific binding partner for the analyte. In a sandwich immunoassay, a labeled conjugate is employed that includes an analyte specific binding member, wherein the labeled conjugate binds to the analyte at a site other than the site to which the other binding member on the substrate binds, wherein the substrate includes a second analyte-specific binding partner. The labeled conjugate is mixed with a sample and the resulting mixture is contacted with the substrate. The analyte will bind to the labeled conjugate and to the other binding member on the substrate, so that the amount of label bound to the substrate will be directly proportional to the amount of analyte present.

Once the sample suspected of containing the analyte has been mixed with the appropriate labeled conjugate, the resulting mixture is contacted with the substrate, which includes a binding pair member appropriate for the analyte being assayed. Enough of the surface must be coated so that a binding reaction can take place between the labeled conjugate and the capture binding member moiety of the substrate such that the label can be detected. Generally, sample volumes introduced into the well will range from about 1 to about 20 microliters, usually about 5 to about 15 microliters, more usually about 5 to about 10 microliters.

After the sample portion has been contacted with the substrate, the sample is incubated for a sufficient time period for binding to occur, that is to form complexes between members of specific binding pairs, e.g. a labeled conjugate binding member and the substrate comprising the bound antigen. The incubation step will typically occur at room temperature, although temperatures in the range of about 10° C. to about 50° C. can be employed. Incubation times will typically range from about 0.5 to about 5 minutes, usually about 0.5 to about 3 minutes, and more usually about 2 minutes. Frequently, the time necessary for introducing a wash solution into the well will suffice for the incubation.

In the case of a competition assay, a number of assay formats are possible. Competition formats include, for example, a one-step assay where the substrate, containing an analyte-specific binding partner, is contacted simultaneously with a sample and a labeled analyte analog. A one-step assay can also be achieved where the analyte analog is on the substrate and the analyte-specific binding partner is labeled with an appropriate reporter molecule. In a two-step competition assay, the sample is mixed with one assay component (e.g., labeled analyte analog) and then after a period of incubation it is mixed with the substrate. As with a one-step assay, either the analyte analog or the analyte-specific binding partner can be located on the substrate with the other being labeled. In an example of the two-step format, the analyte analog, located on the substate, is mixed with the sample for a period of time. A labeled analyte-specific binding partner is then added to the reaction mixture for a second incubation. Regardless of the assay format, the amount of label detected at the detection zone is inversely proportional to the amount of analyte in the sample.

For the most part, the assays, measurements, or tests disclosed herein will depend solely on the substrate and the labeled conjugate for carrying out the immunoassay. In some situations, however, more complex protocols can be employed. For example, instead of having the conjugate binding member labeled directly, the binding member can be indirectly labeled. Where the binding member is an antibody, a labeled anti-antibody can be used, so as to have a universal labeled reagent. Both a labeled conjugate and its reciprocal binding member can be added, where the conjugate competes with the analyte for the reciprocal binding member. The substrate can comprise a capture binding member that captures the reciprocal binding member. For example, the reciprocal binding member can be an antibody and the substrate can be coated with Protein A or G, so as to capture all antibodies. Biotin and avidin can also be used as readily known in the art.

After an incubation step, any labeled conjugate free in the medium is preferably removed from the substrate. Removal of unbound labeled conjugate is conveniently accomplished through introduction of a washing fluid that displaces unbound labeled conjugate. A variety of wash fluids can be used for the washing step. The pH of the wash fluid will be a pH in which the binding pair complexes are stable. Typically, the pH will range from 5 to 9, usually 6 to 8, and more usually about is 7. Depending on the nature of the label of the conjugate, wash solutions may which enhance the label can be employed. For example, the fluorescence of a particular fluorescent label can be enhanced in slightly alkaline or basic solution. In such a case, a buffer having a pH above 7, but usually less than 9, can be employed. Exemplary wash fluids comprise water, buffers, such as phosphate, phosphate buffered saline (PBS), saline solutions, carbonate buffers, and the like. The wash fluid can be introduced to the substrate using any convenient means. Usually the wash fluid will be introduced using the same means as the means used for introduction of the sample. To the extent that the substrate is a reaction well, the wash solution can be taken up a number of times, usually not more than about 6, more usually not more than about 2, or the wash solution can be forced through the well using a syringe, pump or other device.

After the washing step where the unbound labeled conjugate is washed from the substrate, the presence of labeled conjugate remaining bound to the capture binding member on the substrate is detected in a detection step. The detection step can be conducted immediately after the wash step, or can be delayed for a period of time, if necessary. While the detection step for some chemiluminescent labels can be conducted an appropriate wash fluid, the substrate can be dried prior to the detection step to minimize the possibility of interference in the ensuing detection step. The drying may be done by any appropriate means such as air drying, vacuum drying, and the like. If the detection step is to be delayed, the substrate can be stored for a reasonable period of time under ambient or reduced temperature conditions.

When fluorescently-labeled conjugates are used, detection is accomplished by first irradiating a region of the substrate comprising the detection region, followed by measuring the resultant emitted fluorescent signal. Any convenient irradiation means can be employed for providing the appropriate wavelength. Exemplary irradiation means include lasers, light emitting diodes, tungsten lamps and the like. The wavelength of light used in the stimulation means will depend on the particular fluorescent label. Generally, the irradiation light wavelengths will range from 300 to 900 nm, usually from about 350 to 800 nm, and more usually from about 450 to 800 nm. For example, where Cy—5® is the fluorescent label, the wavelength of the irradiation light will range from 630 to 650 nm. The fluorescence from the fluorescently-labeled conjugates present one the substrate can be measured. Measuring the emitted signal is accomplished by detecting the photons emitted in the detection region. Means for measuring fluorescence are commercially available and any convenient fluorescence detector can be used. Various photodiodes, photomultipliers, and the like, can be employed, and in some instances a visual detection will suffice, if a fluorescently-labeled conjugate is used that fluoresces in the visible spectrum.

One well known technique includes the use of a porous carrier matrix capable of providing lateral flow to a liquid test sample and/or liquid reagents. A number of devices are available for such techniques including the reversible flow device described in U.S. Pat. No. 5,726,010, which is incorporated herein by reference in its entirety. Generally, the porous carrier matrix can be selected from any available material having appropriate thickness, pore size, lateral flow rate, and color. Lateral flow refers to liquid flow in which all of the dissolved or dispersed components of the liquid are carried at substantially equal rates and with relatively unimpaired flow laterally through the matrix, as opposed to the preferential retain of one or more components of the liquid, such as a chromatographic separation of the sample. Examples of suitable porous carrier matrices include glass fiber mats, non-woven synthetic mats, sintered particulate structures, cast or extruded matrix materials, or other materials characterized by the presence of adhesion within the material. These materials may be a formed (molded or cast) from open pore structures such as nylon or nitrocellulose. The porous carrier matrix may also be a particulate material such as glass particles or polymer particles.

The porous carrier matrix may be made from a material which has a low affinity for the analyte and test reagents. This is to minimize or avoid pretreatment of the test matrix to prevent nonspecific binding of analyte and/or reagents. However, materials that require pretreatment may provide advantages over materials that do no require pretreatment. Therefore, materials need not be avoided simply because they require pretreatment. Hydrophilic matrices generally decrease the amount of non-specific binding to the matrix.

In one aspect, the porous carrier matrix has an open pore structure with an average pore diameter of 1 to 250 micrometers and, in further aspects, about 3 to 100 micrometers, or about 10 to about 50 micrometers. The matrixes are from a few mils (0.001 in) to several mils in thickness, typically in the range of from 5 or 10 mils and up to 200 mils. The matrix should be translucent to allow for the visualization or photometric determination of the light and or color throughout the thickness of the matrix. The matrix may be backed with a generally water impervious layer, or may be totally free standing.

An example of a suitable porous carrier matrix in which lateral flow occurs is the high density or ultra high molecular weight polyethylene sheet material manufactured by Porex Technologies Corp. of Fairburn, Ga., USA. This material is made from fusing spherical particles of ultra-high molecular weight polyethylene (UHWM-PE) by sintering. This creates a porous structure with an average pore size of eight microns. The polyethylene surface is treated with an oxygen plasma and then coated with alternating layers of polyethylene imine (PEI) and poly acrylic acid (PAA) to create surfactant-free hydrophilic surface having wicking rate of 70 sec/4 cm.

While matrices made of polyethylene have been found to be highly satisfactory, lateral flow materials formed of other olefin or other thermoplastic materials, e.g., polyvinyl chloride, polyvinyl acetate, copolymers of vinyl acetate and vinyl chloride, polyamide, polycarbonate, polystyrene, etc., can be used. Examples of suitable materials include Magna Nylon Supported Membrane from GE Osmonics (Minnetonka, Minn.), Novylon Nylon Membrane from CUNO Inc. (Meriden, Conn.) and Durapore Membrane from Millipore (Billerica, Mass.).

The matrix materials may be slit, cut, die-cut or punched into a variety of shapes prior to incorporation into a device. Examples of alternative shapes of the matrix include circular, square/rectangular-shaped, flattened ellipse shaped or triangularly shaped. Biological reagents may be attached to the materials by any available method, for example, either by passively, diffusively, non-diffusively, by absorption, or covalently, depending upon the application and the assay.

Reagents and sample are contacted with the porous matrix at a sample application zone. The sample application zone is usually upstream of the detection zone so that the liquid reagents flow from the sample application zone to and through the detection zone as a result of the properties of the device for achieving lateral flow. Excess liquid may be captured in an absorbent reservoir. Wash and/or detection reagents may be added, or may be present on-board the device. No specific method of adding the sample and reagents to the device is required. The sample may be applied by dropping the liquid sample and reagents onto the device, or the device may be dipped into the reagents. The sample application zone may optionally include a separate matrix that contains dried reagents that are solubilized upon contact with the sample liquid. For example, the conjugate reagent may be present in a dried form and, when contacted with the sample liquid, become solubilized and participate in the detection reaction. In addition to being present in a separate matrix, the reagents may be present on the porous matrix at a location that allows the solubilization of the reagents by the sample liquid or other liquid such that the reagent can flow to the detection zone and participate in the detection reaction.

The sample application zone may partially or completely overlap the detection zone. However, it has been found that optimum performance of the device is achieved with the sample application zone is laterally spaced from the detection zone. The distance is desired to allow separation of bound and unbound material and thus reduce non-specific binding, for example between the matrix and conjugate reagent. The distance between the sample application zone and the detection zone may depend upon the material of the matrix. In one aspect of the invention using a porous carrier matrix having a lateral flow rate of 70 mm/4 min, the detection zone is about 10 mm from the sample application zone.

The matrix may be pre-wetted, i.e., before the addition of the sample, with a reagent that improves the hydrophobicity of the material. Pre-wetting reagents may be added to any part of the matrix as long as the reagents flow throughout the region including the application zone, the detection zone and the path in between the zones. Examples of pre-wetting reagents include buffers, detergents and low molecular weight carrier proteins, either alone or in a combination of two or three reagents in a premixed form.

Following the addition of the sample and reagents to the device, the label on the conjugate reagent is determined with the method appropriate for the label used. The device should provide an opening or a clear window in the area of the detection zone so that the signals from the labels can be detected any device capable of measuring or detecting light including, for example, photomultiplier tubes (PMTs), avalanche photodiodes (APDs) and charge-coupled devices (CCDs).

In one aspect, the invention employs a porous carrier matrix and a magnetic nanoparticle that is separable from solution with a conventional magnet as described in described in U.S. patent application Ser. No. 11/184,097, filed Jul. 19, 2005, which is incorporated by reference herein in its entirety. As described therein, the magnetic particles can be functionalized to provide a surface for coupling the particles to a molecule or biomolecule. Depending upon the polymer, the surfaces can be activated with a variety of functional groups readily known to those skilled in the art. These groups include, for example, amino, carboxy, alcohol, and aldehyde groups. A variety of attachment chemistries can be used, including covalent attachment or attachment through specific binding partners. Linking molecules may also be employed.

Currently available formats of particles can be broadly classified into unmodified or naked particles, chemically derivatized particles with general specificity ligands (streptavidin, Protein A, etc) and chemically derivatized particles with specific recognition groups such as monoclonal and polyclonal antibodies. Suitable particles with diameters ranging from 50 to 1000 nanometers, and functionalized with a variety surfaces, are available from a number of sources including Micromod Partikeltechnologie GmbH, Rostock-Warnemuende, Germany, Ademtech, Parc scientifique Unitec 1, 4, Allee du Doyen George Brus, 33600 Pessac, France, and EMD Biosciences Inc., Estapor® Microspheres, Division Life Science Products, 1658 Apache Dr., Naperville, Ill. (USA).

In an example of the operation of the device having a porous carrier magnet and a device, a solution containing the sample, a particulate reagent and a detection reagent labeled with an appropriate reporter molecule is applied to the device. The magnet is associated with the porous carrier matrix so the magnetic field will attract and substantially retain the particles at a discreet location on the matrix. An example of such a device is described in U.S. patent application Ser. No. 11/184,097.

The device may include a sample application zone, which may be laterally spaced from the detection zone. The sample application zone may include a separate pad, cup, well or other member that facilitates the application of the sample solution and/or other reagents at a discreet location on the matrix. The sample application zone may also include a conjugate reagent non-diffusively bound the matrix, a separate pad or other member so that the reagent is solubilized by the sample solution upon addition of the solution.

The method and device includes the use of various reagents. These reagents may be added to the device independent of the sample, they may be added to mixtures containing the sample, or they may be stored on-board the device. The reagents include wash reagents for removing unbound reaction materials from the detection zone, detection reagents for detecting the presence of the analyte in the detection zone, and pre-wetting reagents that treat the porous matrix prior to the additional of the sample to reduce non-specific binding.

Wash reagents are well known to those of skill in the art of lateral flow devices. The reagent is capable of removing unbound reactants from the detection zone are appropriate. These reagents are generally a combination of low molecular weight carrier proteins, detergents and preservative. One such reagent is a component of the SNAP® FeLV/FIV Combo Assay (IDEXX Laboratories).

The wash reagent and detection reagents may be stored on-board the device in breakable storage vessels as described in U.S. Pat. No. 5,726,010. Reagents may be delivered to the porous matrix by a reagent delivery wick. The delivery wick may include a lance which serves to both pierce the storage vessels and deliver the reagent to the flow matrix. This linkage facilitates the release of the two stored liquid reagents with a single action. Sequential utilization of the two reagents, i.e., wash reagent followed by detector reagent may also be accomplished. Reagents may also be delivered through automated pipetting stations which dispense reagents onto the porous matrix at defined locations and at defined rates and volumes.

The device of the invention may also include an absorbent reservoir for absorbing the excess sample and reagents. Materials suitable for use as an absorbent reservoir are preferably highly absorbent, provide capacity in excess of the volume of the fluid sample plus the added liquid reagents, and are capable of absorbing liquids from the flow matrix by physical contact as the sole means of fluid transfer between the two materials. A variety of materials and structures are consistent with these requirements. Fibrous structures of natural and synthetic fibers such as cellulose and derivatized cellulose (e.g., cellulose acetate) are preferred for this use. The fibers of the material may be oriented along a particular axis (i.e., aligned), or they may be random. A preferred embodiment of the invention utilizes non-aligned cellulose acetate fibers of density range 0.1 to 0.3 grams per cubic centimeter and void volume of 60 to 95 percent. One such material is R-13948 Transorb Reservoir available from American Filtrona Corporation (Richmond, Va.).

Following the addition of the sample and reagents to the device, the label on the conjugate reagent is determined with the method appropriate for the label used. The device should provide an opening or a clear window in the area of the detection zone so that the signals from the labels can be detected visually or with any device capable of measuring or detecting light including, for example, photomultiplier tubes (PMTs), avalanche photodiodes (APDs) and charge-coupled devices (CCDs). When two labels are employed, the signals from the two labels are detected sequentially or simultaneously. The fluorescent label is detected by exciting the label with the appropriate wavelength and detecting the emission of light. The chemiluminescent signal is read directly following the addition of the enzyme substrate. The same detection device can be used to measure both the fluorescent and the chemiluminescent signals or each signal can be read on independent detection systems. The detection system used may be the same or they may be of different types with the main requirement being that the sensitivity is sufficient to perform the assay.

All of the above embodiments of the invention may be provided as a kit. In one particular example, such a kit would include a device of the invention complete with specific binding reagents, for example, non-immobilized conjugate reagents specific for analyte binding and a solid phase, as well as wash reagent and detector reagent. Positive and negative control reagents may also be included, if desired or appropriate. In addition, other additives may be included, such as stabilizers, buffers, and the like. The relative amounts of the various reagents may be varied widely, to provide for concentrations in solution of the reagents that substantially optimize the sensitivity of the assay. Particularly, the reagents may be provided as dry powders, usually lyophilized, which on dissolution will provide for a reagent solution having the appropriate concentrations for combining with the sample. The kits are usually packaged with instructions for conducting the assay.

To coat the substrate surface for use in the subject method, the surfaces are contacted with a solution comprising the capture binding member. A variety of techniques can be employed, depending in part on the nature of the substrate. With most proteins, particularly antibodies, albumins and globulins, the proteins stick to the surface without covalent bonding, and are stable under the conditions of the immunoassay.

In preparing the substrate surfaces, it can be sufficient to contact the untreated surfaces to a solution comprising the binding reagent. The binding solution is usually a buffered solution having from about $10^{-7}$ to $10^{-3}$ grams of protein/ml. Typically, the protein binding member will be an antibody or fragment thereof for direct assays. For indirect assays, the protein will typically be an analog of the analyte. For the most part, the protein binding member will be an antibody or fragment thereof. Methods of stably coating glass and plastic surfaces are known to persons skilled in the art (see e.g. Harlow, E. & Lane, D. (1988) *Antibodies: A Laboratory Manual*, Cold Spring Harbor Laboratory, Cold Spring Harbor: N.Y.; Harlow, E. & Lane, D. (1999) *Using Antibodies: A Laboratory Manual*, Cold, Spring Harbor Laboratory Press, Cold Spring Harbor: N.Y.; Sambrook, J. et al. (1989) *Molecular Cloning: A Laboratory Manual*, Cold Spring Harbor Laboratory Press, Cold Spring Harbor: N.Y.; and the like). In many instances, where the binding member is not a protein, it can be conjugated to a protein, leaving the binding sites available for binding to the complementary binding member. For example, haptens can be conjugated to a protein that will not interfere with the immunoassay. In this way, an otherwise non-binding analyte or a mimetic or analog thereof can be directly bound to the surface without having to functionalize the surface so as to provide covalent binding of the otherwise non-binding substance.

The surfaces can be coated initially with an agent that enhances the binding of the protein to the surface. Thus, where the binding member does not provide for stable binding to the surface, the surface is activated or functionalized to provide covalent or non-covalent binding of the binding member to the surface. The particular technique used in treating the surface will depend on the composition of the surface and the binding member, e.g. the functional groups available on the binding member for reaction. With surfaces such as plastics, e.g. polystyrene and polyethylene, the surface can be functionalized to provide for reactive amino, carboxy, thio, sulfonyl, hydroxy or other functional groups, by acylation, nitration and reduction, oxidation with ozone, chlorosulfonation, and the like. The specific functional group provided on the surface will depend on the binding member. If the binding member does not naturally comprise a useful available functional group, the binding member can be modified, so as to provide for a functional group that will react with the activated surface, e.g. amino with carboxy, thiol with activated olefin, hydroxy with an activated halogen, and the like. For non-covalent binding of the binding member to the surface, a hydrophobic surface may be provided, that is, a surface that has a long chain alkyl or alkenyl group attached, e.g., through a silicon attaching group.

Glass surfaces can be "functionalized" by using a silicon-based compound having as one part of the compound a silicon moiety that reacts with the glass surface and the other part of the compound being carbon-based that provides a suitable functional group, e.g. alkyl, alkenyl, amino, carboxy, sulfonyl, thiol, activated olefin, such as maleimido, and the like, that will bind with the binding member either covalently or non-covalently (e.g., by van der Waals' forces).

Generally, the coating is done using a silicon-based material that provides a basis for covalently or non-covalently forming a suitable substrate on the interior surface. Suitable silicon-based materials include silanes or siloxanes that bind through the silicon to the glass surface and provide a surface to which an appropriate substrate is bound. Examples of suitable siloxane materials include aminoalkylsiloxanes and alkyl or alkenyltrialkoxysilanes. Conveniently, aminoalkylsiloxanes known in the art can be used, where the aminoalkyl group is of from about 2 to 6 carbon atoms and the alkoxy groups are of from about 1 to 6 carbon atoms. Preferably the silane based material is represented by the formula R—Si(OR$_1$)$_3$, wherein R is an alkyl or alkenyl of about 12 to about 20 carbon atoms and R$_1$ is an alkyl of one to four carbon atoms. A particularly preferred silane-based material is a compound represented by the formula R—Si(OR$_1$)$_3$, wherein R is a straight chain alkyl of 18 carbon atoms and R$_1$ is ethyl. Preferably octadecyltriethoxy silane is chosen as the silane coating material, this is available through Pierce Biotechnology, Inc. (Rockford, Ill.) as AquaSil®.

The level of quantitation possible using the apparatus with the devices described herein depends on the affinity of the capture binding member as previously discussed, detector sensitivity, mathematics used to analyze the signal, and whether standards and/or controls are used and if so on what kinds of standards and/or controls. Generally, affinity of about $10^6$ L/mol can provide sensitivity in the parts per million range and affinity of about $10^9$ L/mol can provide sensitivity in the parts per billion range.

The most basic form of analysis is the determination of the presence of an analyte. For this to occur, the concentration of analyte in the sample must be above some lower limit of quantitation for the immunoassay. Typically, each lot of reagent will have a different associated critical level of signal due to, among other things, variations in the binding affinity of the capture binding member substrate. The apparatus will measure the level of signal and compare it to the pass/fail level for the specific immunoassay corresponding to the concentration of interest.

For quantitation, the signals can be accurately measured using appropriate hardware and software. The area from which the labels are measured is controlled to provide for consistent values. Controls can be employed, where the signal to concentration of the analyte is determined, so that the signal can be directly related to the concentration of analyte in the immunoassay sample. In this manner, both the presence and the amount of analyte in the sample can be determined.

Referring for example to the use of fluorescent labels, plots of normalized fluorescence versus concentration of analyte in parts per billion (ppb) or parts per million (ppm) can be generated. Normalized fluorescence corresponds to the level of signal emitted by a label bound to the surface containing analyte as a percentage of the level of signal emitted by a label bound to the surface of with no analyte, i.e. a blank. Since concentration is inversely proportional to the level of signal for a competitive assay, the curves formed by the plurality of concentration points have a negative slope. If a sample is run on the apparatus, the resulting signal can be compared against the signal generated by a blank run in parallel with the sample. The resulting percentage can be plotted on the appropriate graph and a relative concentration of analyte in sample can be determined. Similar analysis can be employed from chemiluminescent labels. Positive and negative controls can be run with the assays, measurements, or tests disclosed herein.

Various types of spectroscopic hardware can also be employed. Such variations are dictated by the immunoassays, analytes of interest, and other criteria and would be obvious to persons skilled in the art. These variations include, but are not limited to, use of different signal generation means, including, but not limited to, argon lamps, xenon lamps, hydrogen lamps, deuterium lamps, tungsten lamps, nernst glower, nichrome wire, globar, and hollow cathode lamps or other appropriate signal generation means capable of providing emitted signals covering appropriate wavelengths in one or more regions of ultraviolet, visible, near infrared, infrared, and far infrared light; various wavelength selectors including, but not limited to, filters, including interference filters and glass absorption filters, and monochromators, including prism monochromators, such as fluorite prism, fused silica or quartz prism, glass prism, sodium chloride prism, and potassium bromide prism; and gratings; and various signal detection means including, but not limited to, photomultipliers, phototubes, photocells, silicon diodes, and semiconductors.

The following are provided for exemplification purposes only and are not intended to limit the scope of the invention described in broad terms above. All references cited in this disclosure are incorporated herein by reference.

EXAMPLES

Example 1

Preparation of Fluorescent Colloidal Gold Reagent

The following method describes the preparation of a time resolved fluorescent colloidal gold reagent. The procedure described can also be accomplished with other colloids (e.g. silver); other rare earth metals (e.g. Tb, Sm, Dy) other chelating ligands (e.g. NTA) or other synergistic ligands (e.g. TOPO). The procedure can also include the use of fluorescent enhancers (e.g., co-fluorescent ions, non-ionic detergents or water-soluble organic solvents).

Materials:
15 nm colloidal gold (British Biocell Inc.)
NEUTRAVIDIN® (Pierce)
Europium Chloride, fw 258.3 (Aldrich, #42,973-2)
Trioctylphosphine Oxide, fw 386.7 (Aldrich #223301)
3,5,di-fluoro, phenyl, napthyl, propane dione, fw 310.3 (IDEXX Laboratories)
Polyethylene Glycol, fw~15-20,000 (Sigma #P-2263)
Methanol (Sigma #32,241-5)
Dioxane (Sigma #27,053-9)
Borax (Sigma B-3545)

Prepare:
A. 40 mM Borate Stock
   15.25 g Borax dissolved in 800 mL water. QS to 1.0 L.
B. 2 mM Borate Buffer pH 9.0
   50 mL 40 mM Borate added to 800 mL water. pH to 9.0 QS to 1.0 L
C. 10% Poly-Ethylene Glycol in water
   Dissolve 10 g poly-ethylene Glycol in 80 mL water. QS to 100 mL.
D. NEUTRAVIDIN®
   Dissolve NEUTRAVIDIN® in 2 mM Borate. Desalt/Dialyze
   NEUTRAVIDIN® into 2 mM Borate. Determine concentration.
E. 20 mM Europium Chloride in 2 mm Borate
   Dissolve 8.1 mg Europium Chloride in 1.56 mL 2 mM Borate
G. 40 mM Trioctylphosphine Oxide in Methanol
   Dissolve 71.2 mg in 4.6 mL Methanol
H. 20 mM 3,5,di-fluoro, phenyl, napthyl, propane dione in Dioxane
   Dissolve 33.2 mg in 5.35 mL Dioxane
I. 0.3% Poly-Ethylene Glycol in 2 mM Borate
   Add 50 ml 40 mM borate and 30 ml 10% poly-ethylene glycol to 800 ml water.
   Adjust pH to 7.1. QS to 1.0 L
J. 4 mM Europium Chelate in 60% Dioxane/20% Methanol/20% Water.
   To a glass tube add,
   0.2 mL 40 mM Trioctylphosphine Oxide
   0.6 mL 20 mM 3,5,di-fluoro, phenyl, napthyl, propane dione
   0.2 mL 20 mM Europium Chloride Procedure:
To 250 mL of 15 nM colloidal gold,
Add (drop-wise with rapid stirring):
   0.6 mL of 4 mM Europium Chelate—Allow 3 minutes with mixing.
Add (drop-wise with rapid stirring):
   2.0 mL of 11 mg/mL NEUTRAVIDIN®—Allow 3 minutes with mixing.
Add (drop-wise with rapid stirring):
   7.8 mL of 10% Poly-Ethylene Glycol—Allow 15 minutes with mixing.

Centrifuge 15 nm gold (10.5 krpm, for 1 hour) to pellet gold particles. Decant supernatant and re-suspend in 250 mL of 0.3% Poly-Ethylene Glycol. Repeat solvent exchange (wash) twice more with 250 mL of 0.3% Poly-Ethylene Glycol. Finally suspend gold in 5 ml of 0.3% Poly-Ethylene Glycol. The now fluorescent 15 nm gold particles are ready for use.

Example 2

Bioptinylation of 3,5,3'-triiodo-L-thyronine (T3)

Materials:
Biotin-xx-NHS (fw. 567.7) (Sigma#B3290)
3,5,3'-triiodo-L-thyronine (T3) (VWR)
Triethylamine (Aldrich #47,128-3)
DMF (Sigma)

Prepare:
A. 16 mM Biotin in DMF solution
   Dissolve 11.0 mg Biotin-xx-NHS in 1.2 ml DMF
B. 8 mM 3,5,3'-triiodo-L-thyronine (T3) in DMGF solution Dissolve 36.0 mg 3,5,3'-triiodo-L-thyronine (T3) in 6.9 ml DMFC. 10% (717 mM) Triethylamine in DMF solution Dilute 10 µl triethylamine with 90 µl DMF.

Procedure:

To 6.9 ml of 8 mM T3 add 1.15 ml of 16 mM Biotin-xx-NHS with stirring. Allow 90 minutes at RT with mixing.

Example 3

Preparation of Fluorescent Gold Labeled 3,5,3'-triiodo-L-thyronine (T3)

Materials:
Fluorescent 15 nm NEUTRAVIDIN® colloidal gold particles (Example 1)
2.3 mM Biotin-xx-3,5,3'-triiodo-L-thyronine (T3) (Example 2)
Borax (Sigma#B-3545)
Polyethylene Glycol, fw~15-20,000 (Sigma #P-2263)
Prepare:
A. 40 mM Borate Stock
    15.25 g Borax dissolved in 800 mL water. QS to 1.0 L.
B. 2 mM Borate Buffer pH 9.0
    50 mL 40 mM Borate added to 800 mL water. pH to 9.0 QS to 1.0 L
C. 10% Poly-Ethylene Glycol in water
    Dissolve 10 g poly-ethylene Glycol in 80 mL water. QS to 100 mL.
D. 0.3% Poly-Ethylene Glycol in 2 mM Borate
    Add 50 ml 40 mM borate and 30 ml 10% poly-ethylene glycol to 800 ml water.
    Adjust pH to 7.1. QS to 1.0 L
E. 8.2 µM Biotin-xx-T3 in 2 mM Borate Buffer pH 9.0
    Add 0.0323 ml of 2.3 mM Biotin-xx-T3 to 9.0 ml of 2 mM Borate buffer Procedure:

Add 1.0 ml fluorescent 15 nm NEUTRAVIDIN® colloidal gold particles to 9.0 ml of 8.2 µM biotin-xx-T3 on 2 mM borate buffer. Allow 16 hours at RT with mixing.

Centrifuge 15 nm gold (10.5 krpm, for 1 hour) to pellet gold particles. Decant supernatant and re-suspend in 25 mL of 0.3% Poly-Ethylene Glycol. Repeat solvent exchange (wash) twice more with 25 mL of 0.3% Poly-Ethylene Glycol. Finally suspend gold in 1.0 ml of 0.3% Poly-Ethylene Glycol. The now T3 reactive fluorescent 15 nm gold particles are ready for use Example 4

Preparation of Anti-T4 Coated Magnetic Particles

Materials:
200 nM Carboxy Magnetic Particles 3.1% solids (Ademtech #02123)
MES, fw 195.2 (Sigma #M-8250)
Trisma Base, fw 121.1 (Sigma #T-1503)
Monoclonal anti-T4 antibody (Fitzgerald International Industries #M94207)
Triton X-100 (Sigma#X-100)
EDC (1-Ethyl-3-[3-dimethylaminopropyl]carbodiimide hydrochloride), fw 191.7 (Pierce #22980)
BSA, Bovine Serum Albumin (Sigma)
Prepare:
A. 50 mM MES Buffer pH 6.1
    Dissolve 9.76 g MES in 800 mL water. Adjust pH to 6.1. QS to 1.0 L
B. 50 mM Tris Buffer pH 9.0
    Dissolve 6.06 g Tris in 800 mL water. Adjust pH to 9.0 QS to 1.0 L
C. 50 mM Tris/1% Triton X-100 Buffer pH 9.0
    Dissolve 6.06 g Tris in 800 ml water. Add 10 ml Triton X-100. Adjust pH to 9.0 QS to 1.0 L.D.
D. 50 mM EDC in MES Buffer
    Dissolve 34 mg EDC in 3.55 mL MES Buffer.
E. 5% Bovine Serum Albumin (BSA) in MES Buffer.
    Dissolve 5.0 g BSA in 80 ml MES. Adjust pH to 6.1 QS to 100 ml Procedure:

Centrifuge 2 ml of 200 nm particles to pellet solids. Decant supernatant. Suspend particles in 15 ml 50 mM MES Buffer. Repeat solvent exchange (wash) twice more with 15 ml of 50 mM MES Buffer. Finally suspend 200 nm particles in 3.4 mL of 50 mM MES Buffer.

To particles add 6 mg of anti-T4 antibody. To particle antibody mixture add 50 mM EDC. Allow one hour with end over end rotation at RT. Add 0.6 ml of 5% BSA in MES buffer to particles. Allow one hour with end over end rotation at RT. Centrifuge to pellet solids. Decant supernatant. Suspend particles in 15 ml 50 mM Tris/1% Triton buffer. Repeat solvent exchange (wash) twice more with 15 ml of 50 mM Tris/1% Triton buffer.

Centrifuge to pellet solids. Decant supernatant. Suspend particles in 15 ml 50 mM Tris buffer. Repeat solvent exchange (wash) twice more with 15 ml of 50 mM Tris buffer. Finally suspend particles in 6.0 ml 50 mM Tris buffer. Determine % solids and store at 4° C. until required.

Example 5

Analytical Device

A device was prepared using a 0.25 inch diameter, 40 MGOe rare-earth neodymium-iron-boron rod magnet fixed to a Porex matrix, which is a ultra high molecular weight polyethylene sheet material manufactured by Porex Technologies Corp. of Fairburn, Ga., USA. This material is made from fusing spherical particles of ultra-high molecular weight polyethylene (UHWM-PE) by sintering. This creates a porous structure with an average pore size of eight microns. The polyethylene surface is treated with an oxygen plasma and then coated with alternating layers of polyethylene imine (PEI) and poly acrylic acid (PAA) to create surfactant-free hydrophilic surface having wicking rate of 70 sec/4 cm. The matrix was cut into strips about 6.4 mm×100 mm. The magnet and matrix were held in place with a simple device holder.

Example 6

Detection of T4

10 µl of samples having various concentrations of T4 were mixed with 10 µl of SNAP T4 conjugate diluent (IDEXX Laboratories) and 2 µl of monoclonal anti-T4 particles (produced in-house using antibody obtained from Fitzgerald International Industries [#M94207]) at 1.07% solids were incubated together for 5 minutes at 37° C. Following this incubation 2 µl of T3 labeled with fluorescent gold (produced as described above) at a concentration of 42.3 OD and 10 µl of T3-HRP (produced in-house though commercial sources are also available) at 1 µg/ml. The reaction mixture is then incubated for a further 5 minutes. For each reaction mixture, a Porex matrix in a device holder was prewetted for 20 seconds with SNAP® wash reagent. 5 μl of the mixture was spotted onto the Porex matrix approximately 10 mm in front of a 0.25" diameter magnet. The magnet is approximately 20 mm from front tip of Porex matrix. 15 μl of SNAP® wash reagent was spotted a second time. To detect the signals, the matrix was placed in a reading device of either a luminometer or spectrophotometer. PS-atto substrate (Lumingen, Inc.) was flowed over the matrix to detect the chemiluminescent signal. Detection of the fluorescent label was achieved by shining a light source (e.g., a 365 nm LED) at the detection zone above the magnet, and light emitted from the fluorophore on the fluorescent colloidal gold is measured.

Figure 2:
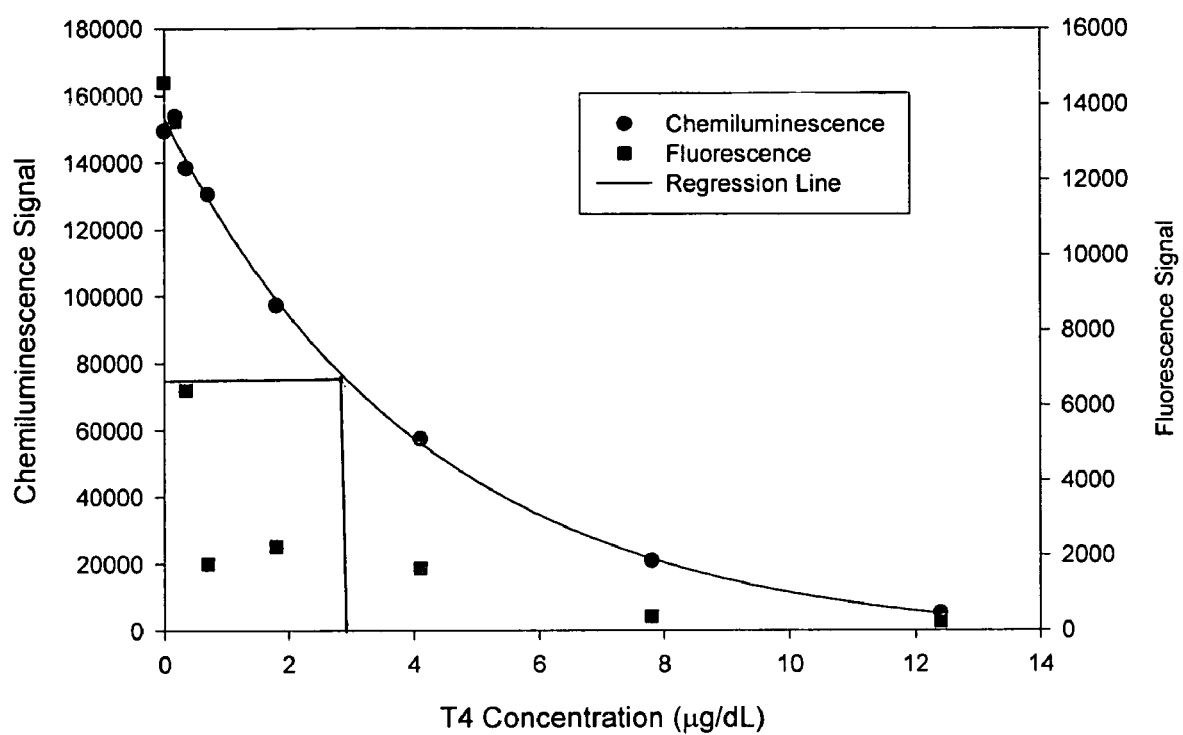
FIG. 2 is a graph showing the same data as FIG. 1 with a regression line for the chemiluminescent signal. Fifty percent of the maximum chemiluminescent signal is 2.6 µg/dL T4.
Figure 3:
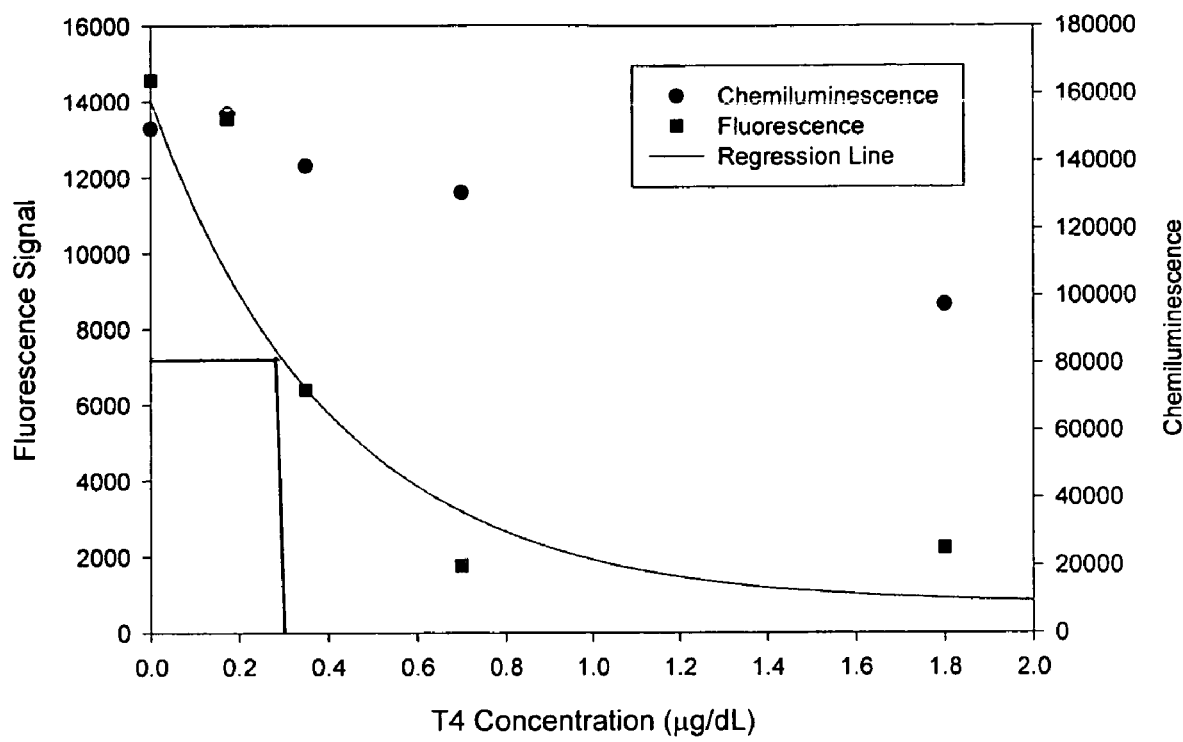
FIG. 3 is a graph showing the same data as FIG. 1 with a regression line for the signal. Fifty percent of the maximum fluorescent signal is 0.35 µg/dL T4.

FIG. 1 shows the amount of both the chemiluminescent signal in the detection zone for the various concentration ranges of T4 and the amount fluorescent signal in the detection zone for the same concentration ranges of T4. FIGS. 2 and 3 show the same data on a different scale to show clearly that fifty percent of the maximum chemiluminescent signal is 2.6 μg/dL T4, and fifty percent of the maximum fluorescent signal is 0.35 μg/dL T4.

Although various specific embodiments of the present invention have been described herein, it is to be understood that the invention is not limited to those precise embodiments and that various changes or modifications can be affected therein by one skilled in the art without departing from the scope and spirit of the invention.

What is claimed is:

1. A method for determining the amount of an analyte in a sample comprising:
    a. providing a quantity of a first specific binding partner for the analyte,
    b. labeling a first aliquot of the quantity of the first specific binding partner with a chemiluminescent label,
    c. labeling a second aliquot of the quantity of the first specific binding partner with a fluorescent label,
    d. mixing the first and second aliquots with the sample,
    e. detecting an amount of association of the fluorescent label with the analyte, detecting an amount of association of the chemiluminescent label with the analyte, wherein detecting the amount of the association of the fluorescent label with the analyte comprises comparing the signal from the fluorescent label associated with the analyte to a standard curve of the concentration of the analyte versus a normalized fluorescence signal, and
    f. determining the amount of the analyte in the sample by correlating the amount of association of the fluorescent label with the analyte and the amount of association of the chemiluminescent label with the analyte to the amount of the analyte in the sample.

2. The method of claim 1 wherein the detecting the association of the fluorescent and chemiluminescent labels with the analyte comprises providing a second specific binding partner for the analyte.

3. The method of claim 1 wherein the sample is mixed with equal amounts of the first and second aliquots.

4. The method of claim 1 wherein detecting the amount of the association of the chemiluminescent label with the analyte comprises comparing the signal from the chemiluminescent label associated with the analyte to a standard curve of the concentration of the analyte versus a normalized chemiluminescent signal.

5. A method of determining the amount of an analyte in a sample over a broad range of potential analyte concentration, the method comprising:
    a. mixing the sample with a specific binding partner for the analyte conjugated to a chemiluminescent label and the specific binding partner for the analyte conjugated to a fluorescent label,
    b. measuring the amount of a signal generated from the fluorescent label that is associated with the analyte and the amount of a signal from the chemiluminescent label that is associated with the analyte,
    c. comparing the amount of the signal generated from the fluorescent label to a standard curve of the amount of the signal from the fluorescent label versus known quantities of the analyte and comparing the amount of the signal generated from the chemiluminescent label to a standard curve of the amount of signal from the chemiluminescent label versus known quantities of analyte; and
    d. determining the amount of the analyte in the sample from comparing step (c).

6. The method of claim 5 wherein the detecting the association of the fluorescent and chemiluminescent labels with the analyte comprises providing a second specific binding partner for the analyte.

7. The method of claim 5 wherein the sample is mixed with equal amounts of the specific binding partner conjugated to the chemiluminescent label and the specific binding partner conjugated to the fluorescent label.

* * * * *